(12) United States Patent
Okuno et al.

(10) Patent No.: US 9,610,053 B2
(45) Date of Patent: Apr. 4, 2017

(54) RADIOGRAPHIC DEVICE

(71) Applicant: SHIMADZU CORPORATION, Nakagyo-ku, Kyoto-shi, Kyoto (JP)

(72) Inventors: Tomoharu Okuno, Kyoto (JP); Hideki Fujii, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 14/759,353

(22) PCT Filed: Jan. 8, 2013

(86) PCT No.: PCT/JP2013/000013
§ 371 (c)(1),
(2) Date: Jul. 6, 2015

(87) PCT Pub. No.: WO2014/108929
PCT Pub. Date: Jul. 17, 2014

(65) Prior Publication Data
US 2016/0073989 A1    Mar. 17, 2016

(51) Int. Cl.
*H05G 1/56* (2006.01)
*A61B 6/00* (2006.01)

(52) U.S. Cl.
CPC ............... *A61B 6/486* (2013.01); *A61B 6/40* (2013.01); *A61B 6/5241* (2013.01); *A61B 6/542* (2013.01); *A61B 6/461* (2013.01); *A61B 6/54* (2013.01)

(58) Field of Classification Search
CPC ........... A61B 6/40; A61B 6/461; A61B 6/486; A61B 6/5241; A61B 6/54; A61B 6/542;
(Continued)

(56) References Cited

U.S. PATENT DOCUMENTS

| 2001/0041832 A1* | 11/2001 | Hirai ..................... A61B 6/06 600/407 |
| 2005/0220269 A1* | 10/2005 | Endo ..................... A61B 6/00 378/114 |
| 2009/0129546 A1* | 5/2009 | Newman .............. A61B 6/4233 378/114 |

FOREIGN PATENT DOCUMENTS

JP      2001-276032       10/2001
JP      2001276032 A  *  10/2001
(Continued)

OTHER PUBLICATIONS

PCT/JP203/000013, International Search Report mailed Mar. 5, 2013, 2 pages—Japanese, 1 page—English.

*Primary Examiner* — Irakli Kiknadze
(74) *Attorney, Agent, or Firm* — Andrew F. Young, Esq.; Lackenbach Siegel, LLP

(57) ABSTRACT

According to this radiography device, by taking images in rapid succession while appropriately obtaining the timing for which an X-ray tube in a rest state should be activated, rapid successive imaging and protection of a radioactive source can both be achieved. That is, in the configuration of the present invention, a time difference is calculated, obtained by subtracting a temporal width of an activation period from a temporal width of an undetectable period, and the time after the time difference has elapsed from the time at which an X-ray is irradiated is determined as the timing for activating the X-ray tube. The temporal width of an undetectable period is the temporal width between the time at which an FPD detects an X-ray once and the time at which the following X-ray can be detected, and the temporal width of an activation period is the temporal width between the start of activation of the X-ray tube to the completion of activation. Thus, while simultaneously activating the X-ray tube and preparing the detector, images can be taken in rapid (Continued)

succession without excessive burden on the X-ray tube and the life of the X-ray tube can be extended.

7 Claims, 14 Drawing Sheets

(58) Field of Classification Search
CPC ....... A61B 6/06; A61B 6/4216; A61B 6/4291;
A61B 6/502; A61B 6/4233; A61B 6/032;
A61B 6/4405; A61B 6/482; A61B 6/501;
A61B 6/505; A61B 5/415; A61B 5/418;
A61B 6/14; A61B 6/4021; A61B 6/485;
A61B 6/507; A61B 6/4035; A61B
6/4007; A61B 6/4028; A61B 6/4441;
A61B 6/469; A61B 6/547; A61B 5/026;
A61B 5/087; A61B 6/12; A61B 6/463;
A61B 6/487; A61B 6/5217; H01J
2235/062; H01J 2235/064; H01J
2235/068
USPC .... 378/98, 115, 98.8, 4, 8; 250/370, 370.01,
250/370.08
See application file for complete search history.

(56) References Cited

FOREIGN PATENT DOCUMENTS

| JP | 2005-312949 | | 11/2005 |
| JP | 2005312949 A | * | 11/2005 |
| JP | 2009-204310 | | 2/2008 |
| JP | 2012070886 A | * | 4/2012 |
| WO | JP 2012-70886 | | 4/2012 |

* cited by examiner

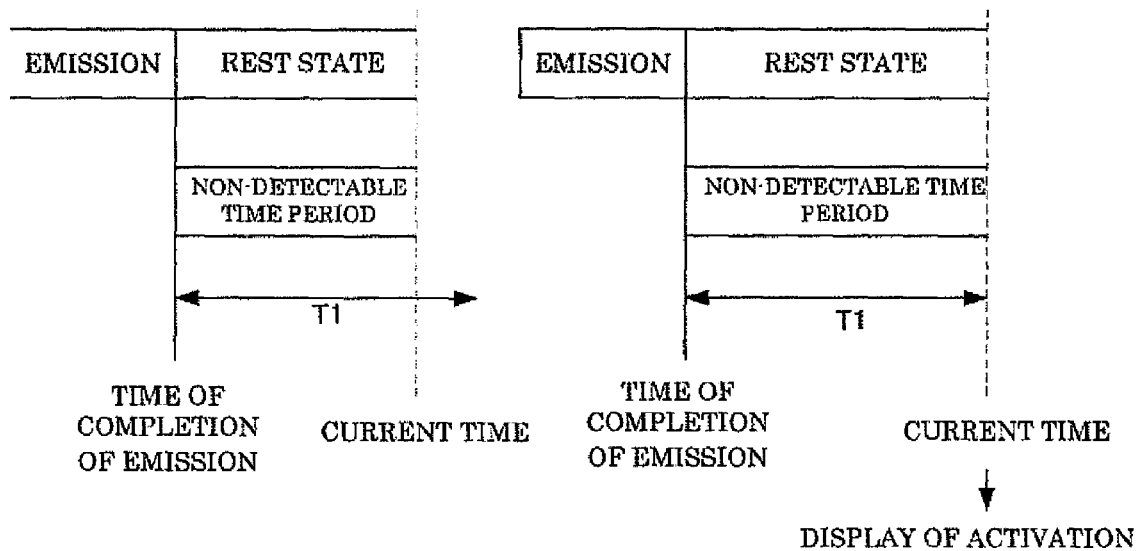

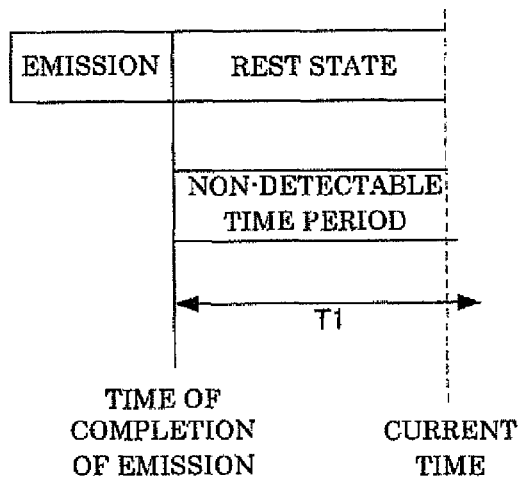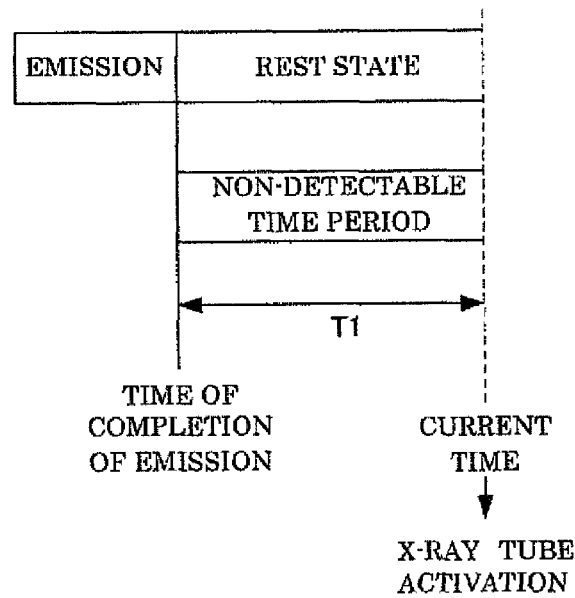

Prior art

RADIOGRAPHIC DEVICE

CROSS REFERENCE TO RELATED APPLICATIONS

This application is the U.S. National Phase under 35 U.S.C. §371, of International Application No. PCT/JP2013/000013, filed on Jan. 8, 2013, the disclosures of which is incorporated fully by reference.

FIGURE SELECTED FOR PUBLICATION

FIG. 1

BACKGROUND OF THE INVENTION

Technical Field

The present invention relates to a radiographic apparatus that emits radiation to a subject to take a fluoroscopic image. More particularly, the present invention is directed to a radiographic apparatus that allows plural-time imaging successively.

Background Art

A medical institution is equipped with a radiographic apparatus that emits radiation to image a subject M. See, for example, Patent Literature 1. Such a radiographic apparatus includes a radiation source 53 emitting radiation, and an FPD 54 detecting radiation, as illustrated in FIG. 13. The subject M stands between the radiation source 53 and the FPD 54.

The radiographic apparatus has a field of view determined from a size of the FPD 54. Consequently, in order to image the subject over an area larger than the size of the FPD 54, plural-time imaging is required while the FPD 54 is moved relative to the subject, as illustrated in FIGS. 14(A), 14(B), and 14(C). When the imaging is performed while the FPD 54 is moved as noted above, an imaging position varies correspondingly. The images obtained at this time contain various FIGs of sites of the subject. Then, combining the images allows an image with a large field of view. Such an imaging method is referred to as long-length radiography.

The plural-time imaging in the long-length radiography should be performed rapidly. That is because a longer time period between the adjacent imaging causes movement of the subject during the imaging, leading to a deviation of FIGs at a joint of the images. Such a method for successive imaging has been devised conventionally.

Examples of conventional imaging method include a method of performing imaging one by one manually. If an operator presses down a startup switch of the radiation source 53, the radiation source 53 in a rest state activates. Then, if the operator presses down an emission-startup switch, the radiation source 53 emits X-rays, and the FPD 54 detects X-rays passing though the subject M. Radiographing a first image is completed in this manner. After the radiography, the radiation source 53 is brought back into a rest state. Thereafter, the FPD 54 is in a standby state until next radiography is ready for performance. Here, no radiography is performable when the FPD 54 is in the standby state. Consequently, a standby period time is provided while the FPD 54 is restored from the standby state.

After the standby period time, if the operator presses down the startup switch of the radiation source 53 again, the radiation source 53 in the rest state activates again for the next radiography. With the radiographic method, in order to take three images, the operator should press down the switch for starting preparation of the radiation source 53 three times, and press down the switch for X-ray emission three times. Such a radiographic method is referred to as a manual mode.

The manual mode mentioned above requires many-time press of the switch by the operator. Accordingly, another imaging mode that allows simple operation of the operator has been devised by adding some ideas to the method mentioned above. In the other imaging method, when the operator presses down the startup switch of the radiation source 53, the radiation source 53 activates and is not changed into the rest state until the radiography completes. Then, if the operator presses down the switch to start emission, X-rays are automatically emitted at given time intervals successively. Here, a time period between anterior and posterior X-ray emission is set longer than that required for restoring the FPD 54 from the standby state. In the radiographic method, the operator is only required to press down the switch one time for preparing the radiation source 53, and one time for X-ray emission even for taking three images. Such an imaging method is referred to as an automatic mode.

PATENT LITERATURE

[Patent Literature 1] Japanese Patent Publication No. 2009-204310A

ASPECTS AND SUMMARY OF THE INVENTION

Technical Problem

However, the conventional configurations mentioned above have the following drawback. That is, with the conventional configurations, rapid radiography and reduction in load of the radiation source 53 is incompatible.

The manual mode allows reduction in load of the radiation source 53. That is because the radiation source 53 is in a rest state for successive imaging in the radiography. It is desirable in the rest state that a filament in the radiation source 53 has low temperatures in terms of protection of the filament. However, in the manual mode, the radiation source 53 activates after the FPD 54 in the standby state is restored. Consequently, the mode is not suitable for successive imaging at short time intervals. That is, in the manual mode, it takes some time for completion of the long-length radiography, leading to possibility to cause a deviation of the FIGs of the subject at the joint upon combining the images. That is because the subject is not ensured to stay at the same position as it takes more time for radiography.

In contrast to this, the automatic mode allows rapid successive imaging. That is because the radiation source 53 is not required to be activated for successive imaging in the radiography, and the FPD 54 having taken the image allows next radiography immediately after being restored from its standby state. On the other hand, in the automatic mode, the radiation source 53 is always in an activated state during successive imaging. As a result, the filament in the radiation source 53 is always exposed to high temperatures. Such a condition causes a shortened life of the filament.

The present invention has been made regarding the noted above facts, and its one object is to provide a radiographic apparatus that allows compatibility between rapid successive imaging and protection of a radiation source.

Solution to Problem

The present invention adopts the following construction for overcoming the above drawback. One embodiment of the present invention discloses a radiographic apparatus comprising; a radiation source that emits radiation and then suspends in a rest state after one-time emission of radiation, a detector that performs detection of radiation passing through a subject and requires time to perform subsequent detection of radiation, an image generator that generates a plurality of images in accordance with each detection signal outputted from the detector every series of radiation emission performed to the subject plural times, an activation instruction input means by which an operator can input an activation instruction to the radiation source in the rest state, an emission instruction input means by which the operator can input a radiation emission instruction to activate the radiation source, a storing means that stores a time width of an activation time period as a time period required for activating the radiation source and a time width of a non-detectable time period that the detector requires until the subsequent detection of radiation is performable after the detector performs the detection of radiation, a difference time calculating means that calculates difference time as a difference obtained by subtracting the time width of the activation time period from the time width of the non-detectable time period, and a determining means that determines that a timing to activate the radiation source in the rest state has arrived after the difference time elapsed from the radiation emission if the operator provides the radiation emission instruction via the emission instruction input means.

[Operation and Effect] With the radiographic apparatus of the present invention, the images can be taken successively while a timing to activate the radiation source in the rest state is acquired appropriately. That is, with the configuration of the present invention, the difference time is calculated by subtracting the time width of the activation time period from the time width of the non-detectable time period. Then, the time after the difference time elapsed from the radiation emission is determined as a timing to activate the radiation source. Here, the time width of the non-detectable time period is a time width from the detection of radiation to subsequent performable detection of radiation by the detector. The time width of the activation time period is a time width from beginning to completion of activation of the radiation source. The radiation source is activated at the timing with the present invention, whereby end of the non-detectable time period conforms to end of the activation time period of the radiation source. This allows rapid successive imaging while the activation of the radiation source and preparation of the detector are performed simultaneously. In addition, the radiation source is brought into a rest state every radiation emission so that an excessive load to the radiation source can be suppressed and, the life of the radiation source can be prolonged.

Moreover, it is preferable that the radiographic apparatus according to the embodiment of the present invention further includes a notifying means. The notifying means notifies the operator of arrival of the timing to provide the instruction via the activation instruction input means in accordance with the determination by the determining means after the emission instruction input means provide the radiation emission instruction.

[Operation and Effect] The foregoing configuration is a concrete example of the radiographic apparatus according to the present invention. The operator is notified of the timing determined by the determining means, causing the radiation source to activate at an appropriate timing only in accordance with the notification.

Moreover, the radiographic apparatus according to the embodiment of the present invention further preferably comprises a radiation source controller. The radiation source controller provides the activation instruction to the radiation source in accordance with the determination by the determining means after the emission instruction input means provides the radiation emission instruction.

[Operation and Effect] The foregoing configuration is a concrete example of the radiographic apparatus according to the present invention. The radiation source controller provides the activation instruction to the radiation source in accordance with the determination by the determining means. This causes the radiation source to be activated at an appropriate timing under automatic control regardless of the operator's instruction.

Moreover, it is preferable that the notifying means of the radiographic apparatus provides visible display to the operator.

Moreover, it is preferable that the notifying means of the radiographic apparatus produces a sound to the operator.

[Operation and Effect] The foregoing configuration is a concrete example of the radiographic apparatus according to the present invention. The notifying means according to the embodiment of the present invention is variable flexibly depending on an environment in which the apparatus is installed.

Moreover, it is preferable that the notifying means of the radiographic apparatus according to the embodiment of the present invention counts down the timing before the difference time elapses if the emission instruction input means provides the radiation emission instruction.

[Operation and Effect] The foregoing configuration is a concrete example of the radiographic apparatus according to the present invention. The notifying means performs notification that the timing for the determining means has arrived through the count down, whereby the operator can provide the instruction more easily.

Moreover, the radiographic apparatus according to the embodiment of the present invention further includes a long-length image generator that generates a long-length image by combining a series of images taken while the detector is moved relative to the subject.

[Operation and Effect] The foregoing configuration is a concrete example of the radiographic apparatus according to the present invention. The present invention is suitable for the long-length radiography mentioned above.

Advantageous Effects of Invention

With the radiographic apparatus of the present invention, successive imaging is performable while a timing to activate the radiation source in the rest state is acquired appropriately. That is, with the configuration of the present invention, the difference time is calculated by subtracting the time width of the activation time period from the time width of the non-detectable time period. Then, the time after the difference time has elapsed from the radiation emission time is determined as a timing to activate the radiation source. Here, the time width of the non-detectable time period is a time width from the detection of radiation to subsequent performable detection of radiation by the detector. The time width of the activation time period is a time width from beginning to completion of activation of the radiation source. This allows rapid successive imaging while the activation of the radiation source and preparation of the detector are performed simultaneously, allowing suppression of excessive load to the radiation source and a prolonged life of the radiation source.

BRIEF DESCRIPTION OF THE DRAWINGS

FIGS. 5(A), 5(B) are timing charts illustrating an operation of the X-ray apparatus according to Embodiment 1.

FIGS. 10(A), 10(B) are timing charts illustrating an operation of the X-ray apparatus according to Embodiment 1.

DESCRIPTION OF THE PREFERRED EMBODIMENTS

The following describes embodiments of the present invention. X-rays in the embodiment correspond to radiation in the present invention. An FPD is the abbreviation of a flat panel detector.

Embodiment 1

<Whole Construction of X-Ray Apparatus>

Figure 1:
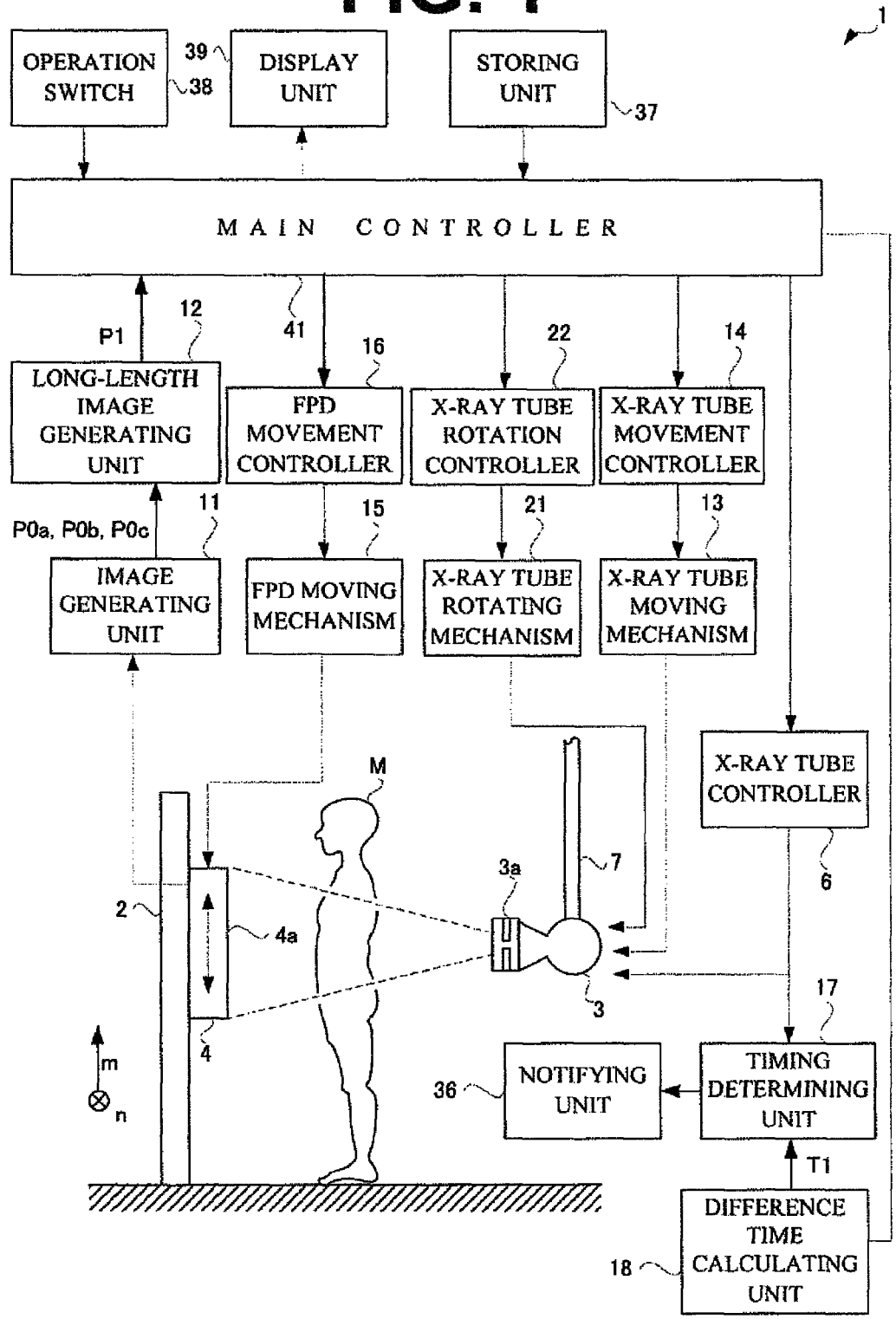
FIG. 1 is a function block diagram illustrating an X-ray apparatus according to Embodiment 1 of the present invention.

The following firstly describes an X-ray apparatus 1 according to Embodiment 1. Here, the configuration of Embodiment 1 adopts an improvement over a conventional manual mode. The X-ray apparatus 1 images a standing subject M. As illustrated in FIG. 1, the X-ray apparatus 1 includes a strut 2 extending vertically from the floor, an X-ray tube 3 emitting X-rays, an FPD 4 supported on the strut 2, and a suspending holder 7 extending vertically and held on the ceiling. The suspending holder 7 suspendingly holds the X-ray tube 3. The X-ray tube 3 corresponds to the radiation source in the present invention. The FPD 4 corresponds to the detecting means in the present invention.

A collimator 3a is provided for restricting an area of X-rays emitted from the X-ray tube 3. An operator adjusts a leaf of the collimator 3a, and correspondingly an emission area of X-rays becomes larger or smaller.

The FPD 4 is slidable vertically relative to the strut 2. The suspending holder 7 is also expandable vertically. A position of the X-ray tube 3 in a vertical direction is variable with expansion of the suspending holder 7. An FPD moving mechanism 15 between the above elements 2 and 4 moves the FPD 4 vertically relative to the strut 2. Consequently, the vertical direction is a moving direction m of the X-ray tube 3 and the FPD 4. An FPD movement controller 16 controls movement of the FPD moving mechanism 15. The FPD 4 can detect X-rays passing through the subject M.

The following describes movement of the X-ray tube 3. The X-ray tube 3 is moved by an X-ray tube moving mechanism 13 provided in the suspending holder 7. An X-ray tube movement controller 14 controls the X-ray tube moving mechanism 13. The X-ray tube moving mechanism 13 moves the X-ray tube 3 (1) in the vertical direction (moving direction m), (2) in directions approaching and away from the FPD 4, and (3) in a horizontal direction S orthogonal to an emission direction from the X-ray tube 3 to the FPD 4 (orthogonal direction n: in FIG. 1, a plane-passing direction, a body-side direction of the subject M). The suspending holder 7 expands and contracts when the X-ray tube 3 is moved in the vertical direction. Here, the emission direction, the moving direction, and the orthogonal direction n are each orthogonal to one another.

An X-ray tube rotating mechanism 21 rotates the X-ray tube 3. The X-ray tube rotating mechanism 21 has a rotary axis around which the X-ray tube 3 is rotated. The rotary axis is orthogonal to the central axis of X-ray beams from the X-ray tube 3 and the vertical direction. Moreover, the rotary axis passes a focus of the X-ray tube 3. An X-ray tube rotation controller 22 controls the X-ray tube rotating mechanism 21.

An X-ray tube controller 6 controls a tube voltage and a tube current of the X-ray tube 3 and an irradiation time of X-rays. The X-ray tube controller 6 controls the X-ray tube 3 so as to output radiation with a given tube current, a tube voltage, and a pulse width. Parameters, such as the tube current, are stored in a storing unit 37. The X-ray tube controller 6 corresponds to the radiation source controller in the present invention. The storing unit 37 corresponds to the storing means in the present invention.

The FPD 4 has a detecting surface 4a detecting X-rays (see FIG. 1). The detecting surface 4a is disposed in the X-ray apparatus 1 while erecting in the vertical direction. This achieves effective radiography to the standing subject M. The detecting surface 4a faces to an X-ray emitting hole of the X-ray tube 3. In other words, the detecting surface 4a is disposed along a plane formed by two directions, i.e., the orthogonal direction n and the moving direction m. The detecting surface 4a is rectangular, one side thereof corresponding to the orthogonal direction n and the other side orthogonal to the one side corresponding to the moving direction m.

An image generating unit 11 constructs detection data outputted from the FPD 4 to generate an original image P0 with a projection image of the subject M appearing therein. The image generating unit 11 generates a plurality of images in accordance with detection signals every X-ray emission in series performed plural times to the subject M, the detection signals each being outputted from the FPD 4. The image generating unit 11 corresponds to the image generator in the present invention.

The X-ray apparatus 1 of Embodiment 1 can perform so-called long-length radiography. In the radiography, a plurality of original images P0 is combined to generate one large image. Here, the X-ray apparatus 1 performs radiography three times while a relative positional relationship between the X-ray tube 3 and the FPD 4 is maintained. See FIG. 2. That is, first radiography is performed when the X-ray tube 3 and the FPD 4 are located in a position denoted by dashed-dotted lines. Second radiography is performed when the X-ray tube 3 and the FPD 4 are located in a position denoted by dotted line. Third radiography is performed when the X-ray tube 3 and the FPD 4 are located in a position denoted by solid lines. The original images P01 taken through the first, the second and the third radiographies are denoted by signs P0a, P0b, and P0c, respectively, for differentiation.

Figure 3:
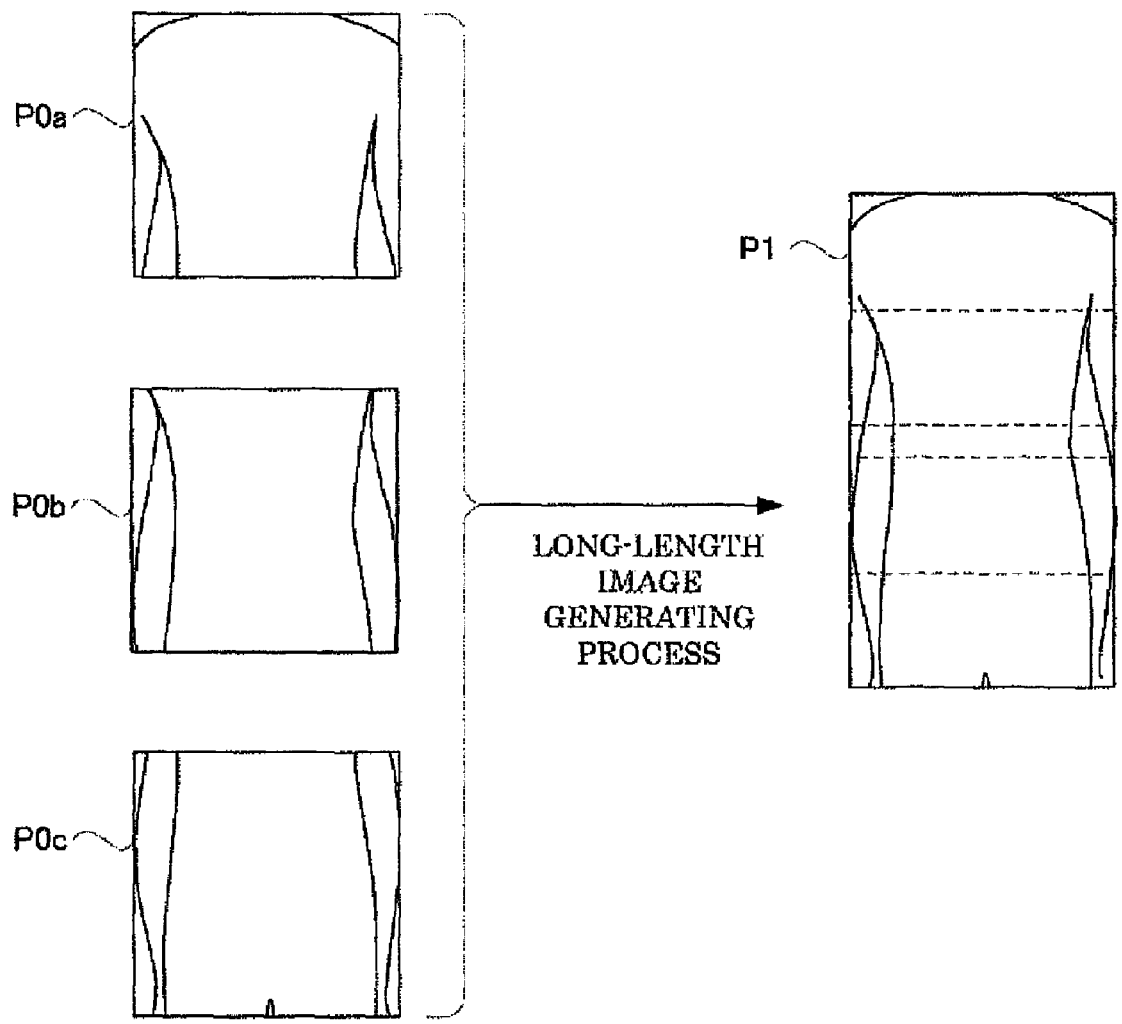
FIG. 3 is a schematic view illustrating a long-length radiography according to Embodiment 1.

As illustrated in FIG. 3, a long-length image generating unit 12 combines the original images P0a, P0b, P0c having different sites of the subject M appearing therein to generate one long image P1. That is, the long-length image generating unit 12 combines a series of images taken while the subject M is moved relative to the FPD 4. The long-length image generating unit 12 corresponds to the long-length image generating means in the present invention.

An operation switch 38 inputs various instructions by the operator. The operator can provide the activation instruction of the X-ray tube 3 and the X-ray emission instruction via the operation switch 38. The operation switch 38 is a dual-position switch. The first position is used for inputting the activation instruction of the X-ray tube 3 by the operator. The second position is used for inputting the X-ray emission instruction by the operator. In this manner, the operation switch 38 inputs the activation instruction of the X-ray tube 3 in a rest state by the operator, and inputs the X-ray emission by the operator to the activated X-ray tube 3. The operation switch 38 corresponds to the emission instruction input means and the activation instruction input means in the present invention.

If the operator inputs the activation instruction of the X-ray tube 3, the X-ray tube controller 6 initiates an activation of the X-ray tube 3 in a rest state. Here, the rest state of the X-ray tube 3 represents a condition in which a filament in the X-ray tube 3 that ejects electrons is kept at low temperatures. Moreover, a state in which the activation of the X-ray tube 3 completes represents a condition in which the filament is kept at high temperatures. The X-ray tube 3 allows the X-ray emission only in the condition in which the activation is completed. The X-ray tube 3 is changed to its rest state after one-time X-ray emission.

A timing determining unit 17, a difference time calculating unit 18, and a notifying unit 36 are the most characteristic feature in Embodiment 1, and detailed description thereof is to be made later. The notifying unit 36 corresponds to the notifying means in the present invention. The difference time calculating unit 18 corresponds to the difference time calculating means in the present invention.

<Most Characteristic Feature in Embodiment 1>

The most characteristic feature in Embodiment 1 is that the operator can provide the activation instruction of the X-ray tube 3 at an appropriate timing in Embodiment 1. The following firstly describes how the long-length radiography is performed in Embodiment 1.

Figure 4A:
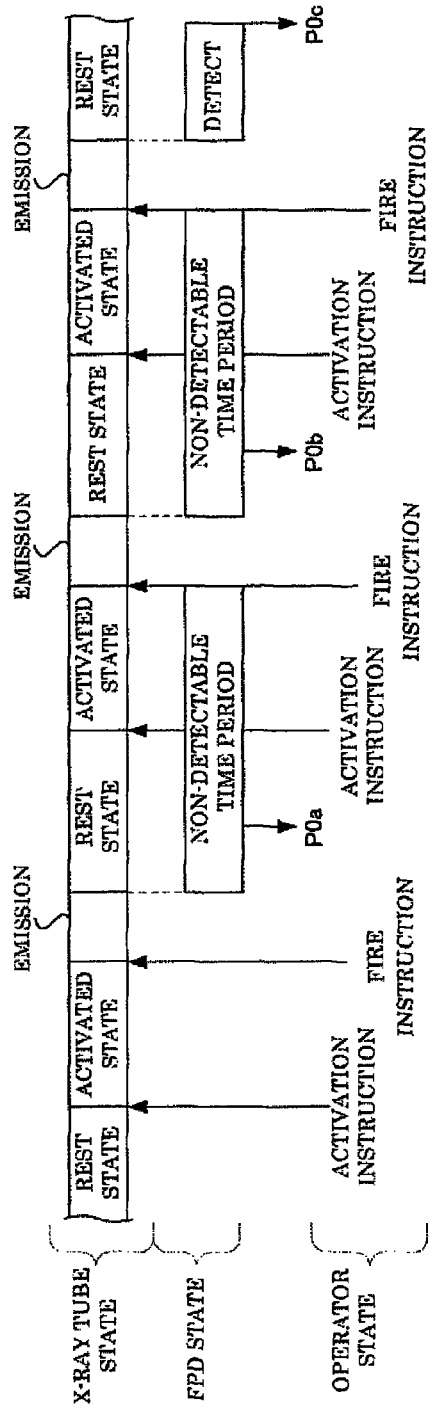
FIGS. 4(A), 4(B) are timing charts illustrating an operation of the X-ray apparatus according to Embodiment 1.
Figure 4B:
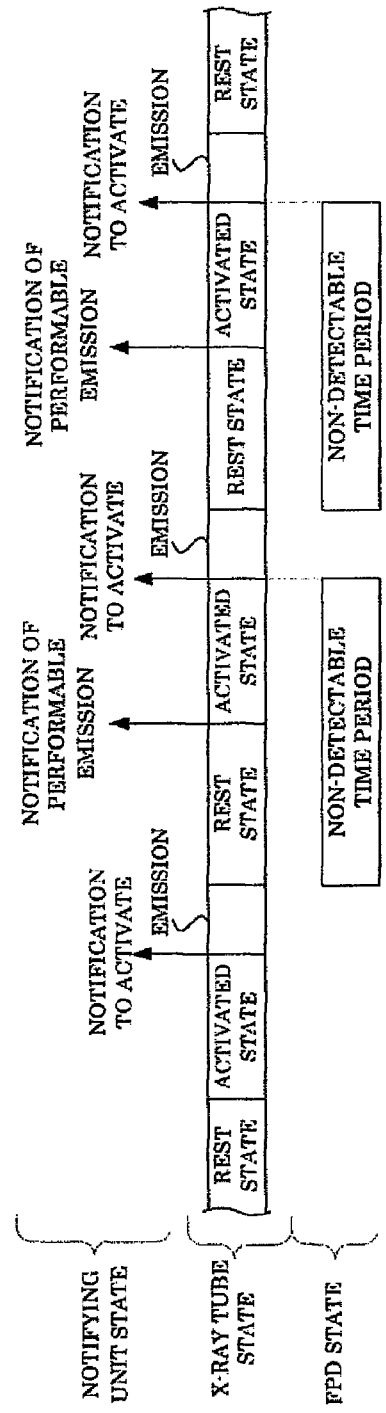

FIGS. 4(A), 4(B) illustrate on the upper thereof a timing chart of performing the long-length radiography with the X-ray apparatus 1 according to Embodiment 1. An upper sequence indicates a state of the X-ray tube 3, and a lower sequence indicates a state of the FPD 4. In the upper of FIGS. 4(A), 4(B), the original images P0a, P0b, and P0c illustrated in FIG. 3 are taken in this order.

The following describes in detail the radiography above. Prior to activation of the long-length radiography, the X-ray tube 3 is in a rest state. Accordingly, the X-ray tube 3 cannot emit X-rays under this state. Then, the operator provides the activation instruction of the X-ray tube 3 via the operation switch 38. The X-ray tube controller 6 controls the X-ray tube 3 so as to be activated immediately after receipt of the instruction from the operator. However, it takes some time from the activation of the X-ray tube 3 to complete the activation. The time period is referred to as an activation time period.

After the activation time period has elapsed, the operator provides the emission instruction via the operation switch 38. Then, the X-ray tube controller 6 provides the X-ray emission instruction to the X-ray tube 3, and correspondingly the X-ray tube 3 emits X-rays. The X-rays are incident through the subject M on the FPD 4. The FPD 4 detects the X-rays, and transmits a detection signal to the image generating unit 11. In this manner, a first original image P0a is generated. After completion of the X-ray emission, the X-ray tube 3 is brought back into a rest state where the temperature of the filament in the X-ray tube 3 decreases.

Here, the FPD 4 requires some time for subsequent detection of X-rays after one-time detection of X-rays passing through the subject M. When X-rays are emitted continuously regardless of such the state, a generated image may contain a false image. Although the detection signal has already been transmitted to the image generating unit 11, an residual image of the subject M does not completely disappear and remains on the FPD 4 immediately after being subjected to incident X-rays. Such a residual image disappears by itself after some time has elapsed from the incidence of the X-rays. When radiography is performed before the residual image on the FPD 4 disappears, the residual image upon anterior radiography may be superimposed on an image generated upon posterior radiography.

Consequently, radiography should be delayed for successive imaging until the FPD 4 having detected X-rays one time allows detection of X-rays again. A time period during which the FPD 4 cannot detect X-rays is referred to as a non-detectable time period. When radiography is performed in the non-detectable time period of the FPD 4, the false image mentioned above may appear in the image to be generated.

After the original image P0a is generated, the operator provides the activation instruction of the X-ray tube 3 via the operation switch 38. Then, the instruction by the operator is transmitted to the X-ray tube controller 6. The X-ray tube controller 6 activates the X-ray tube 3 changed into a rest state. After the activation time period has elapsed, the operator provides the emission instruction via the operation switch 38. At this time, the non-detectable time period of the FPD 4 has already ended, and accordingly no false image appears in the original image P0b. In this manner, a second original image P0b is generated. After completing the X-ray emission, the X-ray tube 3 is brought back into a rest state where the temperature of the filament in the X-ray tube 3 decreases. Simultaneously, the FPD 4 enters into the non-detectable time period.

After the original image P0b is generated, the operator provides the activation instruction of the X-ray tube 3 via the operation switch 38. Then the X-ray tube controller 6 controls the X-ray tube 3 in a rest state so as to be activated again. After the activation time period has elapsed, the operator provides the emission instruction via the operation switch 38. At this time, the non-detectable time period of the FPD 4 has already ended. Accordingly, no false image appears in the original image P0c to be generated. In this manner, a third original image P0c is generated.

As noted above, the operator provides the activation instruction of the X-ray tube 3 at an appropriate timing. Consequently, activation of the X-ray tube 3 and restore of the FPD 4 under a non-detectable state overlap each other sequentially. This causes a shorter interval of X-ray emission by the operator than that in the conventional manual mode that activates the X-ray tube 3 after the FPD 4 is restored. Consequently, Embodiment 1 can obtain an image with a high resolution and with no false image appearing therein despite the shortened interval of X-ray emission.

Here, the operator allows providing the activation instruction to the X-ray tube 3 at an appropriate timing since the X-ray apparatus 1 notifies the operator as to the timing to activate the X-ray tube 3 via the notifying unit 36. Accordingly, the operator can perform appropriate radiography as illustrated on the upper of FIG. 4 by merely providing the instruction in accordance with the notification from the X-ray apparatus 1.

FIG. 4(B) illustrates a timing chart indicating a timing of notification to the operator from the X-ray apparatus 1. The X-ray apparatus 1 performs the notification via the notifying unit 36 to activate the X-ray tube 3 during the non-detectable time period of the FPD 4 after the X-ray emission. In addition, the X-ray apparatus 1 performs notification via the notifying unit 36 that X-ray emission is performable when the activation of the X-ray tube 3 completes. Such time conforms to time when the non-detectable time period of the FPD 4 ends in the second and third radiography. In Embodiment 1, radiography of the original image P0 is performed three times. Accordingly, notification to activate the X-ray tube 3 is provided two times, and notification that X-ray emission is performable is provided three times. Here, the first activation of the X-ray tube 3 merely means activation of the long-length radiography, and thus is any timing that the operator can determine optionally. Consequently, there is no need to provide notification to activate the X-ray tube 3 in the first radiography.

For specific operation of the notifying unit 36, it is conceivable to display contents of the notification on a monitor of the notifying unit 36. Moreover, the notifying unit 36 may be formed by a speaker, and the contents of the notification may be transmitted to the operator with sounds. As noted above, the notifying unit 36 allows notification to the operator by the visible display or the sounds.

<Determination of Timing of Notification>

The following describes how to determine a timing of notification. The timing determining unit 17 in FIG. 1 determines a timing of notification. FIGS. 5(A), 5(B) illustrate operations of notification to activate the X-ray tube 3 by the timing determining unit 17. That is, the timing determining unit 17 is in a standby state until given time period T1 has elapsed from completion of the X-ray emission for radiography. Thereafter, the timing determining unit 17 controls the notifying unit 36 so as to provide display indicating activation of the X-ray tube 3. FIG. 5(A) illustrates a timing chart when the given time period T1 has not elapsed from the completion of the X-ray emission. At this time, the timing determining unit 17 never controls the notifying unit 36 so as to providing the display noted above. The timing determining unit 17 corresponds to the determining means in the present invention.

FIG. 5(B) illustrates the right time thereof when the given time period T1 has elapsed from the completion of the X-ray emission. At this time, the timing determining unit 17 controls the notifying unit 36 as to providing the above display. Correspondingly, the notifying unit 36 provides the display to the operator to activate the X-ray tube 3, and accordingly, the operator provides the activation instruction of the X-ray tube 3 via the operation switch 38 to the X-ray apparatus 1. As noted above, the timing determining unit 17 determines that the timing to activate the X-ray tube 3 in a rest state has arrived after the difference time elapsed from the X-ray emission when the operator provides the emission instruction to the operation switch 38.

Here, the time after the given time period T1 has elapsed from the completion of the X-ray emission is in the middle of the non-detectable time period of the FPD 4, as illustrated in FIG. 5(B). The X-ray tube 3 activates before the non-detectable time period of the FPD 4 ends. Accordingly, the time when the activation of the X-ray tube 3 completes conforms to the time when detection by the FPD 4 is performable.

The difference time calculating unit 18 concretely determines the given time period T1 necessary for operation of the timing determining unit 17. The difference time calculating unit 18 calculates the given time period T1 from a time width of the activation time period of the X-ray tube 3 determined in advance and a time width of the non-detectable time period of the FPD 4 also determined in advance. That is, the difference time calculating unit 18 calculates the given time period T1 by subtracting a time period representing a length of the activation time period of the X-ray tube 3 from a time period representing a length of the non-detectable time period. In other words, the difference time calculating unit 18 calculates difference time as a difference obtained by subtracting the time width of the activation time period of the X-ray tube 3 from the time width of the non-detectable time period of the FPD 4. Specifically, the time width of the non-detectable time period of the FPD 4 is around 5 seconds, and the time width of the activation time period of the X-ray tube 3 is around 1 second.

Figure 6:
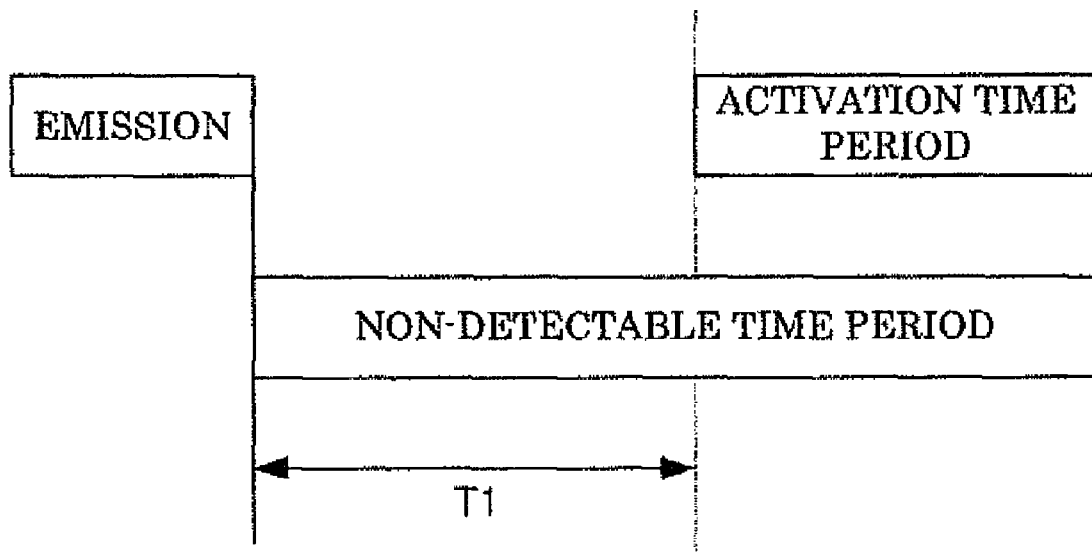
FIG. 6 is a timing chart illustrating an operation of the X-ray apparatus according to Embodiment 1.

The given time period T1 calculated by the difference time calculating unit 18 is a time period representing how the non-detectable time period of the FPD 4 is longer than the activation time period of the X-ray tube 3, as illustrated in FIG. 6. The given time period T1 also represents suspended time for activating the X-ray tube 3 from completion of the X-ray emission so as for the completion of the activation of the X-ray tube 3 to conform to end of the non-detectable time period of the FPD 4. A storing unit 37 stores set values of the given time period T1. The timing determining unit 17 reads out one of the set values as necessary from the storing unit 37 for operation.

The following summarizes the above operation. That is, after receiving the X-ray emission instruction (emission instruction) via the operation switch 38, the notifying unit 36 notifies the operator that the timing has arrived to provide the instruction via the operation switch 38 in accordance with the determination by the timing determining unit 17.

Figure 7:
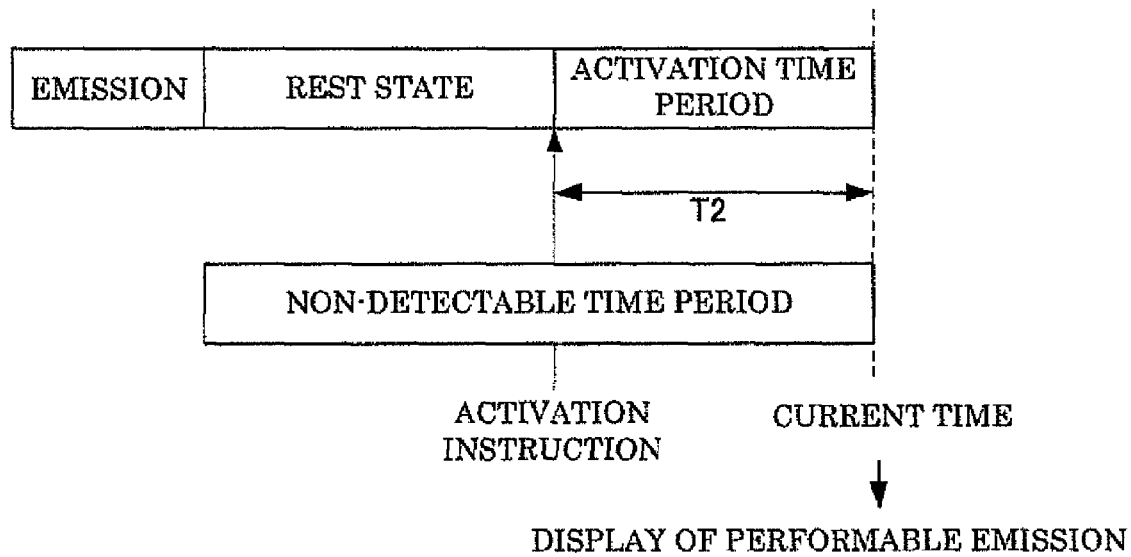
FIG. 7 is a timing chart illustrating an operation of the X-ray apparatus according to Embodiment 1.

FIG. 7 illustrates operation of the timing determining unit 17 when the notifying unit 36 notifies the operator that the X-ray emission is performable. See FIG. 4(B). That is, the timing determining unit 17 provides the activation instruction of the X-ray tube 3 to the operator, and correspondingly the X-ray tube 3 is in a standby state until a given time period T2 has elapsed from the activation of the X-ray tube 3. Then the timing determining unit 17 controls the notifying unit 36 as to providing display indicating that the X-ray emission is performable after the give time period T2 has elapsed from the activation of the X-ray tube 3. Accordingly, the notifying unit 36 notifies the operator of the performable X-ray emission. Then, the operator correspondingly provides an instruction to emit X-rays via the operation switch 38 to the X-ray apparatus 1. The time after the given time period T2 has elapsed from the time when the operator provides the activation instruction of the X-ray tube 3 is also time when the activation of the X-ray tube 3 completes, and the non-detectable time period of the FPD 4 ends. Here, the given time period T2 is set so as to have the time width of the activation time period of the X-ray tube 3. The storing unit 37 stores set values of the given time period T2. The timing determining unit 17 reads out one of the set values as necessary from the storing unit 37 for operation.

<Cooperation of X-Ray Tube Controller and Timing Determining Unit>

The timing determining unit 17 receives information on control of the X-ray tube 3 sequentially from the X-ray tube controller 6. The timing determining unit 17 determines time when the X-ray emission completes and time when the activation instruction of the X-ray tube 3 is provided from the information received from the X-ray tube controller 6.

<Effect of Embodiment 1>

Figure 8:
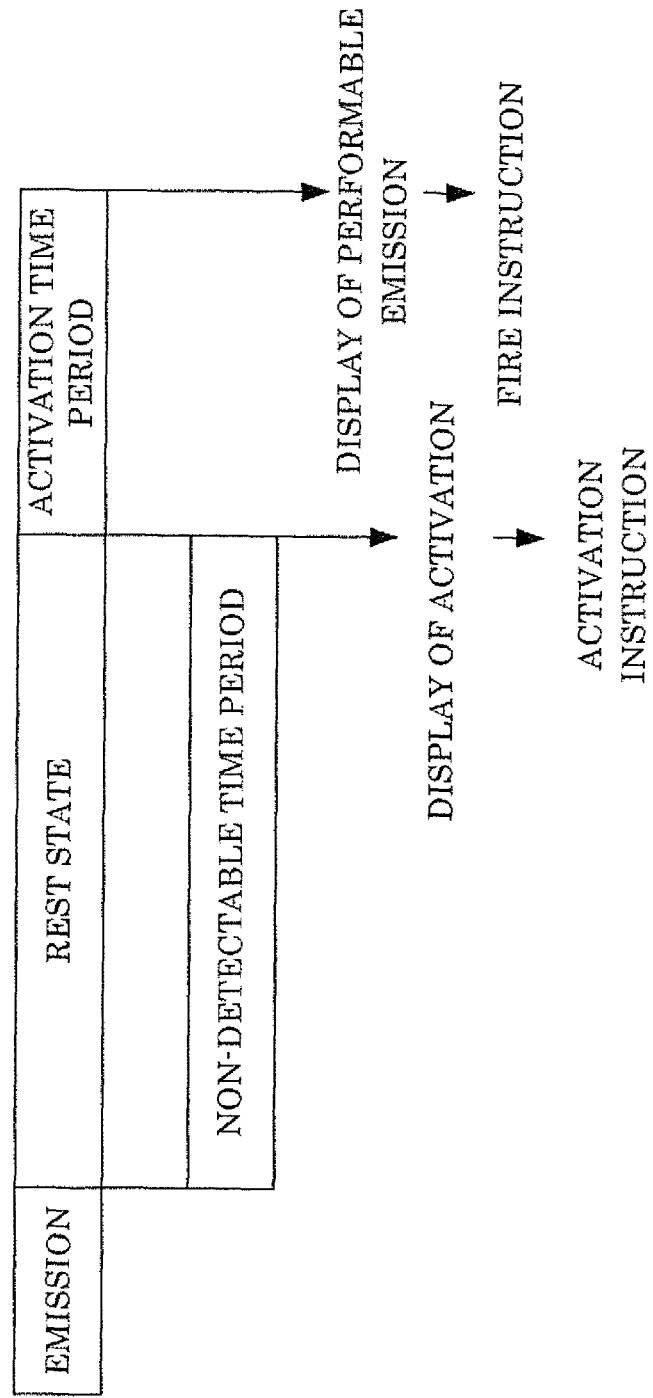
FIG. 8 is a timing chart illustrating an effect of Embodiment 1.

The following describes an effect by the timing determining unit 17 configured as mentioned above. FIG. 8 illustrates a conventional configuration. In the conventional configuration, an instruction to activate the X-ray tube 3 is displayed at time when the non-detectable time period of the FPD 4 ends. Accordingly, the operator activates the X-ray tube 3 after the non-detectable time period of the FPD 4 ends. The following is revealed from comparison between FIG. 8 and the upper of FIG. 4 illustrating Embodiment 1. That is, in Embodiment 1, the FPD 4 that does not allow detection of X-rays is restored simultaneously with the activation of the X-ray tube 3. In contrast to this, in the configuration illustrated in FIG. 8, the operations are performed in series. As noted above, Embodiment 1 achieves shorter time necessary for the posterior X-ray emission after the anterior X-ray emission than that in the conventional manual mode.

<Other Elements of X-Ray Apparatus>

The following describes other elements of the X-ray apparatus 1. The storing unit 37 stores various parameters, such as an incidence area to be mentioned later and an imaging distance, used for X-ray radiography in association with types of radiography. As illustrated in FIG. 1, the X-ray apparatus 1 includes a main controller 41 controlling en bloc the components 6, 14, 16, 11, 18, and 22. The main controller 41 has a CPU, and provides each unit executing various programs. The above components may be divided into arithmetic units that perform their functions. A display unit 39 is provided for displaying the long image P1 obtained through radiography. The storing unit 37 stores the time width of the activation time period required for activating the X-ray tube 3, and the time width of the non-detectable time period required until posterior X-ray detection is performable after the one-time X-ray detection by the FPD 4.

<Actual Long-Length Radiography>

Figure 2:
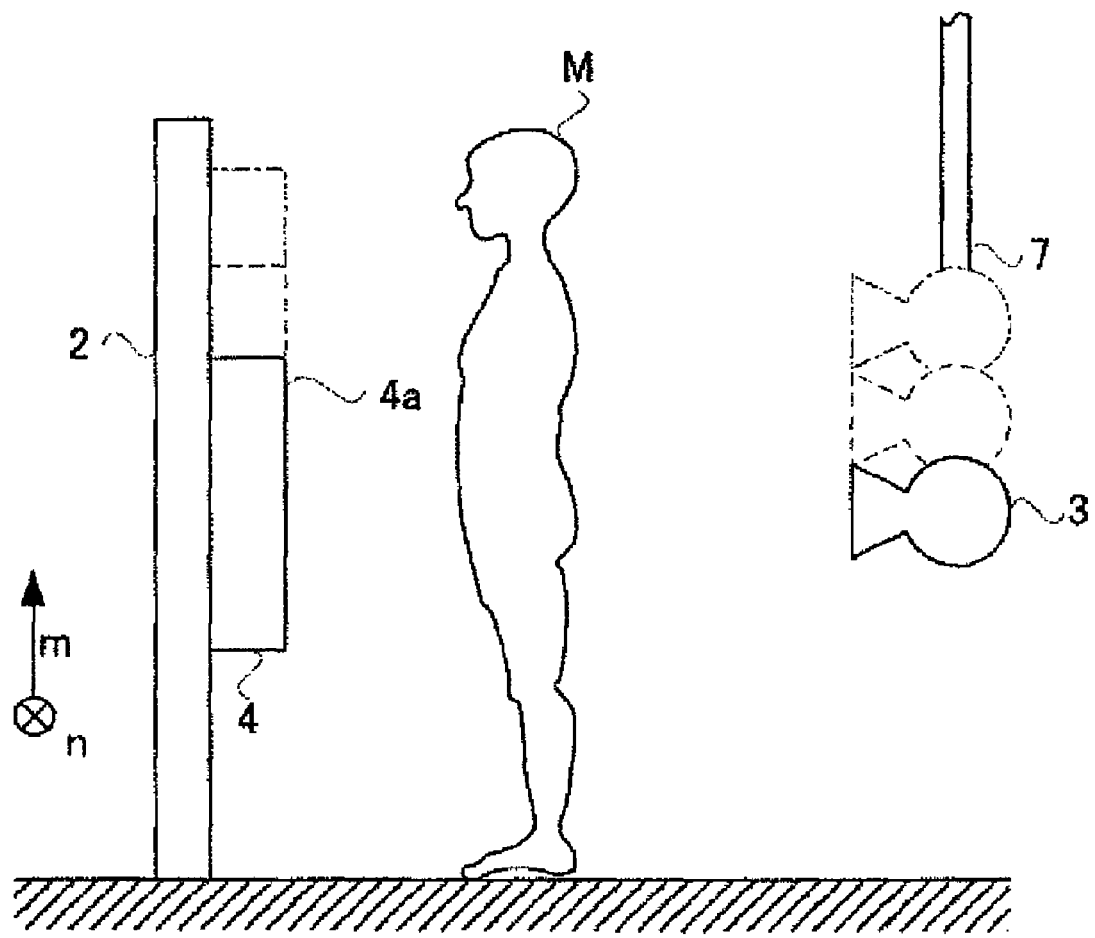
FIG. 2 is a schematic view illustrating a long-length radiography according to Embodiment 1.

The following describes how the long-length radiography is actually performed. In Embodiment 1, when the X-ray apparatus 1 performs long-length radiography, the operator provides the activation instruction of the X-ray tube 3 and the X-ray emission instruction at the timings as described in FIG. 4. The X-ray tube controller 6 controls the X-ray tube 3 in accordance with the instructions. As illustrated in the upper of FIG. 4, the X-ray tube 3 and the FPD 4 are moved immediately after the X-ray emission completes. The movement has already been described with FIG. 2. That is, the X-ray tube 3 and the FPD 4 located at the positions denoted by dashed-dotted lines in FIG. 2 are moved to the positions denoted by dotted line after X-ray emission for taking an original image P0a, and then an original image P0b is obtained. Then after the X-ray emission for taking the original image P0b, the X-ray tube 3 and the FPD 4 in the positions denoted by dotted lines are moved to the positions denoted by solid lines, whereby an original image P0c is obtained. The obtained original images P0a, P0b, and P0c are transmitted to the long-length image generating unit 12. The long-length image generating unit 12 combines the original images P0a, P0b, and P0c to generate a long image P1. The display unit 39 displays the generated long image P1, whereby the long-length radiography completes.

As noted above, with the X-ray apparatus according to Embodiment 1, successive imaging is performable while the timing to activate the X-ray tube 3 in a rest state is acquired appropriately. That is, with the configuration of Embodiment 1, the difference time is calculated by subtracting the time width of the activation time period from the time width of the non-detectable time period, and the time after the difference time has elapsed from the X-ray emission is determined as a timing to activate the X-ray tube 3. Here, the time width of the non-detectable time period is a time width from when the FPD 4 detects X-rays one time to when posterior X-ray detection is performable. The time width of the activation time period is a time width from activation to completion of the activation of the X-ray tube 3. The X-ray tube 3 activates at the timing with Embodiment 1, whereby end of the non-detectable time period of the detector conforms to end of the time period for activating the X-ray tube 3. This allows rapid successive imaging while the activation of the radiation source and preparation of the detector are performed simultaneously. In other words, Embodiment 1 achieves shorter time necessary for posterior emission of X-rays after the anterior emission of X-rays than that in the conventional manual mode.

As noted above, notification of the timing determined by the determining unit 17 is provided to the operator, whereby the operator allows activating the X-ray tube 3 at an appropriate timing only in accordance with the notification.

The X-ray tube controller 6 is provided so as to cause the X-ray tube 3 to perform the activation instruction in accordance with the determination by the timing determining unit 17. This allows activating the X-ray tube 3 at an appropriate timing under automatic control regardless of the instruction by the operator.

Embodiment 2

The following describes an X-ray apparatus 1 according to Embodiment 2. The X-ray apparatus 1 according to Embodiment 2 is similar to Embodiment 1 in its configuration. Accordingly, description about the configuration of Embodiment 2 common to that of Embodiment 1 is to be omitted. The configuration of Embodiment 2 is improvement of the conventional automatic mode.

Embodiment 2 differs from Embodiment 1 in that long-length radiography for the second and subsequent times is performed automatically. That is, the X-ray apparatus 1 in Embodiment 2 allows successive radiography of a plurality of images by merely one-time instruction to activate the X-ray tube 3 and one-time instruction to emit X-rays by an operator.

Figures 9A, 9B:
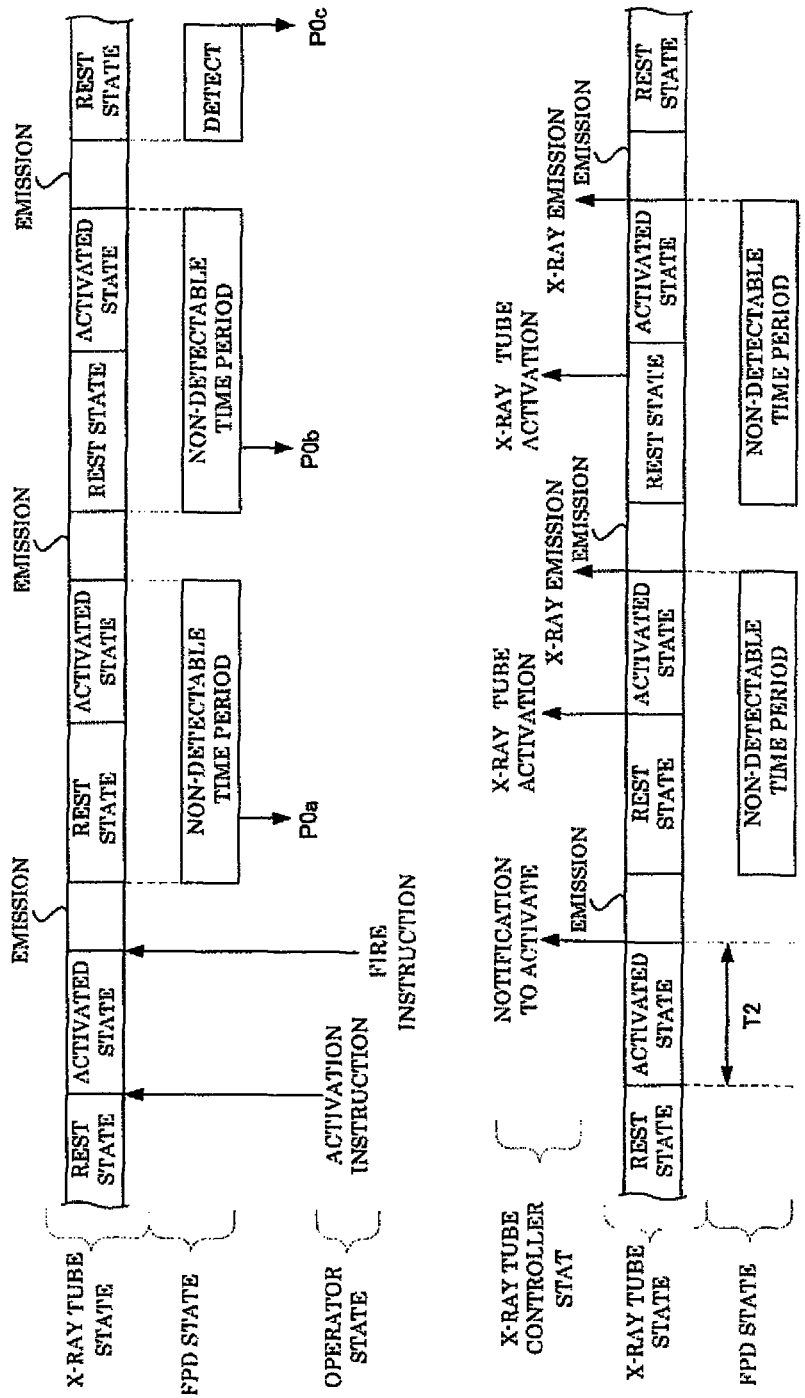
FIGS. 9(A), 9(B) are timing charts illustrating an operation of the X-ray apparatus according to Embodiment 1.

FIGS. 9(A), 9(B) illustrate a timing chart illustrating performance of long-length radiography with the X-ray apparatus 1 of Embodiment 2. An upper sequence 9(A) of the drawing indicates a state of the X-ray tube 3, and a lower sequence (9B) indicates a state of the FPD 4. In the upper portions of FIGS. 9(A), 9(B), the original images P0a, P0b, and P0c illustrated in FIG. 3 are taken in this order.

The following described in detail the radiography above. Prior to activation of the long-length radiography, the X-ray tube 3 is in a rest state. Accordingly, the X-ray tube 3 cannot emit X-rays under this state. Then, the operator provides the activation instruction of the X-ray tube 3 via the operation switch 38. The X-ray tube controller 6 controls the X-ray tube 3 so as to be activated immediately after receipt of the instruction from the operator.

After the activation time period elapsed, the operator provides the emission instruction via the operation switch 38. Then, the X-ray tube controller 6 provides the X-ray emission instruction to the X-ray tube 3, and correspondingly the X-ray tube 3 emits X-rays. The X-rays are incident through the subject M on the FPD 4. The FPD 4 detects the X-rays, and transmits a detection signal to the image generating unit 11. In this manner, a first original image P0*a* is generated. After completing of the X-ray emission, the X-ray tube 3 is brought back into a rest state where the temperature of the filament in the X-ray tube 3 decreases.

After the original image P0*a* is generated, the X-ray tube controller 6 activates again the X-ray tube 3 changed into a rest state. After the activation time period elapsed, the X-ray tube controller 6 provides the X-ray emission instruction to the X-ray tube 3, At this time, the non-detectable time period of the FPD 4 has already ended, and accordingly no false image appears in the original image P0*b*. In this manner, a second original image P0*b* is generated. After completion of X-ray emission, the X-ray tube 3 is brought back into a rest state where the temperature of the filament in the X-ray tube 3 decreases. Simultaneously, the FPD 4 enters into the non-detectable time period.

After the original image P0*b* is generated, the X-ray tube controller 6 causes the X-ray tube 3 to provide the activation instruction. Then the X-ray tube 3 in a rest state is activated again. After the activation time period elapsed, the X-ray tube controller 6 provides the X-ray emission instruction to the X-ray tube 3. At this time, the non-detectable time period of the FPD 4 has already ended. Accordingly, no false image appears in the original image P0*c* to be generated. In this manner, a third original image P0*c* is generated.

As noted above, the X-ray tube controller 6 provides the activation instruction of the X-ray tube 3 at an appropriate timing, whereby rapid successive imaging is performable as before without activating the X-ray tube 3 all the time. Consequently, Embodiment 2 allows performing radiography of an image having high resolution and with no false image appearing therein under suppressed degradation of the X-ray tube 3.

Here, the X-ray tube controller 6 allows providing the activation instruction of the X-ray tube 3 at an appropriate timing since the timing determining unit 17 provides notification of a timing to activate the X-ray tube 3 to the X-ray tube controller 6. The X-ray tube controller 6 allows performing appropriate radiography as illustrated in the upper of FIG. 9 by merely providing the instruction to the X-ray tube 3 in accordance with the notification from the timing determining unit 17. In other words, the X-ray tube controller 6 provides the activation instruction to the X-ray tube 3 in accordance with the determination by the timing determining unit 17 after the emission instruction via the operation switch 38.

FIGS. 9(A), 9(B) illustrate a timing chart indicating a timing of notification to the X-ray tube 3 by the X-ray tube controller 6. The X-ray tube controller 6 activates the X-ray tube 3 via the timing determining unit 17 after the X-ray emission and in the middle of the non-detectable time period of the FPD 4. In addition, the X-ray tube controller 6 causes the X-ray tube 3 to emit X-rays via the timing determining unit 17 at the time when the activation of the X-ray tube 3 is completed. Such time conforms to time when the non-detectable time period of the FPD 4 ends in the second and third radiography. In Embodiment 2, radiography of the original image P0 is performed three times. Accordingly, notification to activate the X-ray tube 3 is provided two times, and notification that X-ray emission is performable is provided three times. Here, the first activation of the X-ray tube 3 is performed through the operator's instruction. Consequently, there is no need for the timing determining unit 17 to provide notification to activate the X-ray tube 3 in the first radiography.

FIGS. 10(A), 10(B) illustrate operations of the timing determining unit 17 at the timing of activating the X-ray tube 3 according to Embodiment 2. See the lower of FIGS. 9(A), 9(B). The operation of the timing determining unit 17 is almost equal to that of Embodiment 1 described with FIG. 5. Specifically, FIG. 10(A) illustrates a timing chart when given time period T1 has not elapses from the completion of the X-ray emission. At this time, the timing determining unit 17 never controls the notifying unit 36 to provide the display noted above. FIG. 10(B) illustrates a timing when the given time period T1 has elapsed from the completion of the X-ray emission. At this time, the timing determining unit 17 provides the notification to the X-ray tube controller 6 to activate the X-ray tube 3.

Here, the time after the given time period T1 has elapsed from the completion of the X-ray emission is in the middle of the non-detectable time period of the FPD 4, as illustrated in FIG. 10(B). The X-ray tube 3 activates before the non-detectable time period of the FPD 4 ends. Accordingly, the time when the activation of the X-ray tube 3 completes conforms to the time when detection by the FPD 4 is performable. The end of the time periods conforms to each other in the same manner as that in Embodiment 1.

The difference time calculating unit 18 calculates the given time in the same manner as that in Embodiment 1 described with FIG. 7, and thus description thereof is to be omitted. The given time period T1 calculated by the difference time calculating unit 18 is a time period representing how the non-detectable time period of the FPD 4 is longer than the activation time period of the X-ray tube 3. The given time period T1 also represents delay time of activating the X-ray tube 3 from completion of the X-ray emission so as for the completion of the activation of the X-ray tube 3 to conform to end of the non-detectable time of the FPD 4. The storing unit 37 stores set values of the given time period T1. The timing determining unit 17 reads one of the set values as necessary from the storing unit 37 for operation.

Figure 11:
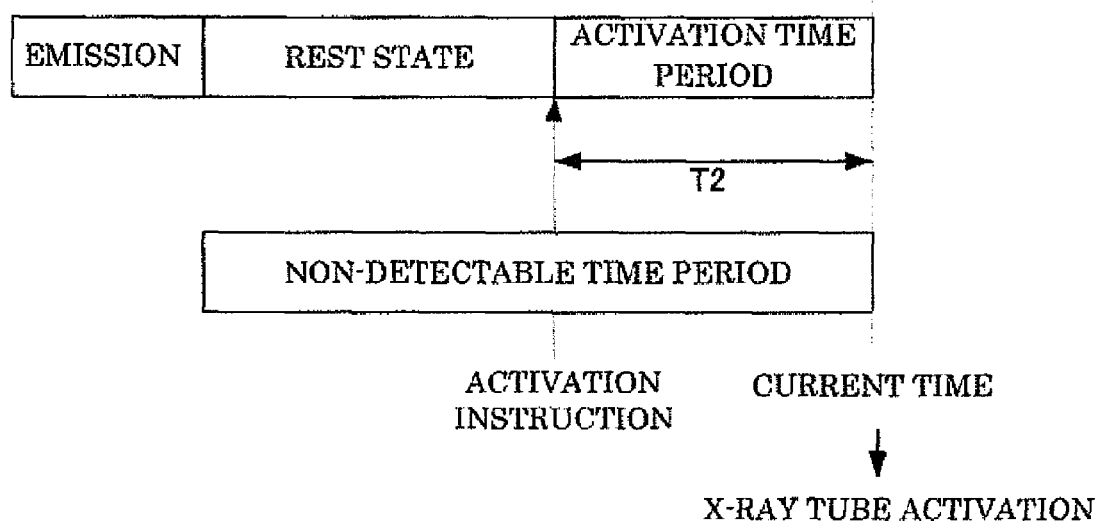
FIG. 11 is a timing chart illustrating an operation of the X-ray apparatus according to Embodiment 1.

FIG. 11 illustrates operation of the timing determining unit 17 when the X-ray tube controller 6 causes the X-ray tube 3 to emit X-rays. See FIG. 9(B). That is, the timing determining unit 17 is in a standby state until a given time period T2 elapses from activation of the X-ray tube 3 by the X-ray tube controller 6. Then the timing determining unit 17 provides notification of emitting X-rays to the X-ray tube controller 6 after the given time period T2 has elapsed from the activation of the X-ray tube 3. Correspondingly, the X-ray tube controller 6 causes the X-ray tube 3 to emit X-rays. The time after the given time period T2 has elapsed from the time of providing the activation instruction of the X-ray tube 3 is also time when the activation of the X-ray tube 3 completes, and the non-detectable time period of the FPD 4 ends. Here, the given time period T2 is set so as to have the time width of the activation time period of the X-ray tube 3 determined in advance. The storing unit 37 stores set values of the given time period T2. The timing determining unit 17 reads one of the set values as necessary from the storing unit 37 for operation.

The notifying unit 36 may operate in association with the timing determining unit 17. That is, the timing determining unit 17 may notify the operator via the notifying unit 36 that the X-ray emission is performable before radiography of the original image P0. In this case, the timing determining unit 17 activates operation from the time when the X-ray tube 3 activates activation in accordance with the activation instruction of the X-ray tube 3 via the operation switch 38 by the operator. Specifically, the timing determining unit 17 controls the notifying unit 36 so as to provide display indicating that the X-ray emission is performable after the given time period T2 has elapsed from the time. See FIG. 9(B). Consequently, rapid and accurate long-length radiography is performable with only the emission instruction by the operator in accordance with the notification.

<Cooperation of X-Ray Tube Controller and Timing Determining Unit>

The timing determining unit 17 receives information on control of the X-ray tube 3 sequentially from the X-ray tube controller 6. The timing determining unit 17 determines time when the X-ray emission completes and time when the activation instruction of the X-ray tube 3 is provided from the information received from the X-ray tube controller 6.

<Effect of Embodiment 2>

Figure 12:
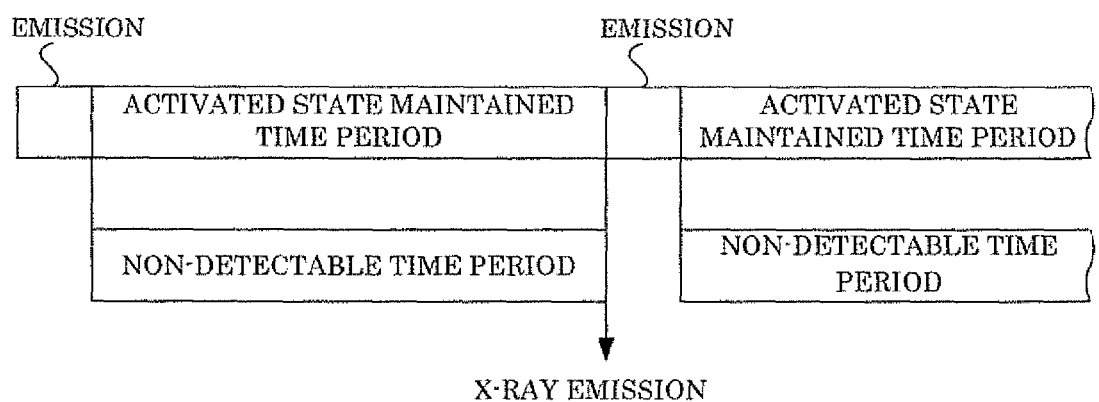
FIG. 12 is a timing chart illustrating an effect of Embodiment 1.
Figure 13:
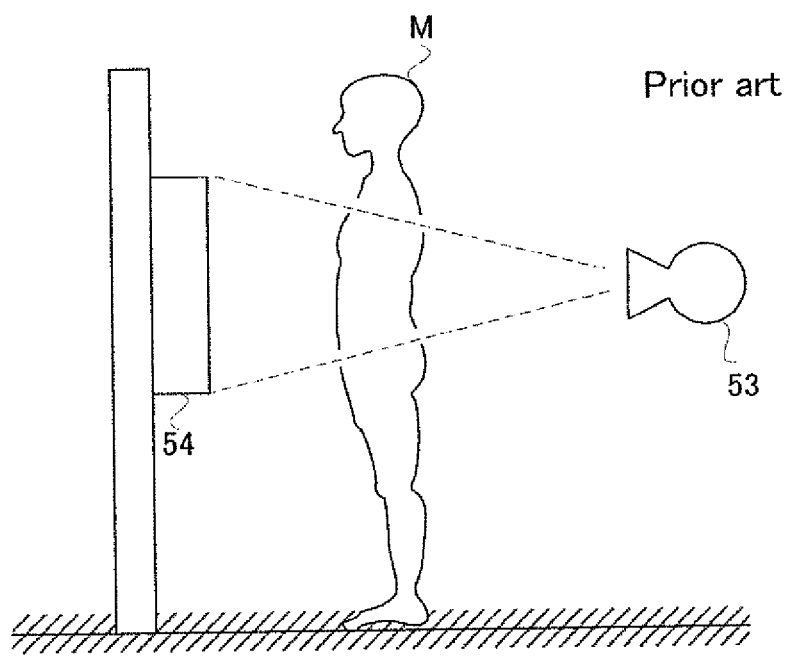
FIG. 13 is a schematic view illustrating a conventional X-ray apparatus.
Figures 14A, 14B, 14C:
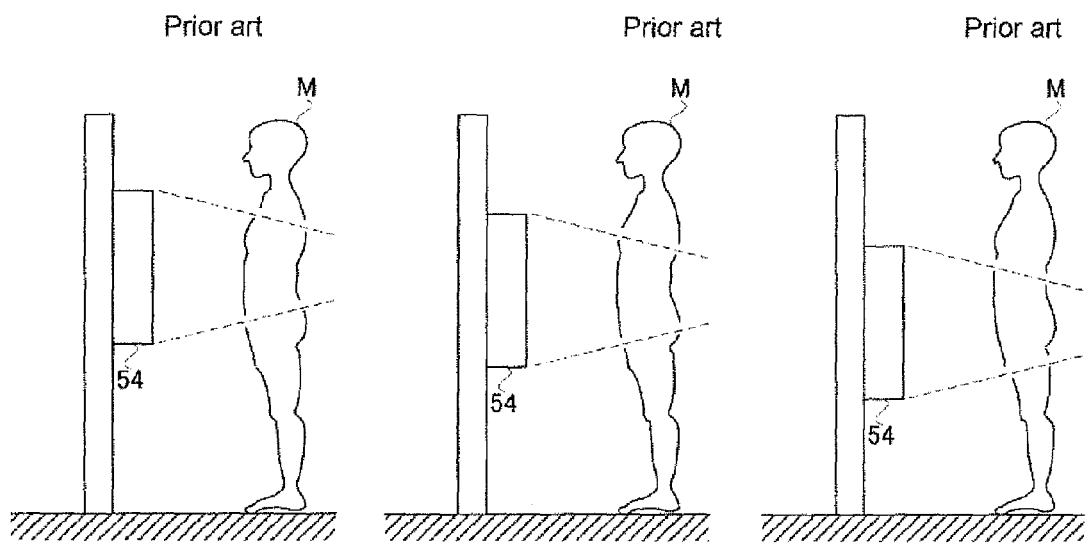
FIGS. 14(A), 14(B), and 14(C) are schematic views illustrating a conventional X-ray apparatus.

The following describes an effect by the timing determining unit 17 configured as mentioned above. FIG. 12 illustrates a conventional configuration. The following is revealed from comparison between FIG. 12 and FIG. 9(A) illustrating Embodiment 2. That is, in Embodiment 2, the X-ray tube 3 is in a rest state during X-ray emission. In contrast to this, in the conventional automatic mode in FIG. 12, the X-ray tube 3 is always in an activated state once the successive imaging is activated. Accordingly, in the conventional automatic mode, the filament in the X-ray tube 3 is always kept at high temperatures, causing ready damages on the filament. As noted above, Embodiment 1 achieves a longer life of the X-ray tube 3 than in the conventional type.

The other configuration of the X-ray apparatus 1 in Embodiment 2 is equal to that in Embodiment 1, and thus description thereof is to be omitted.

<Actual Long-Length Radiography>

The following describes how the long-length radiography is actually performed. In Embodiment 2, when the X-ray apparatus 1 performs long-length radiography, the operator provides the activation instruction of the X-ray tube 3 and the emission instruction at the timings as described in FIG. 9. The X-ray tube controller 6 controls the X-ray tube 3 in accordance with the instructions. As illustrated in FIG. 9(A), the X-ray tube 3 and the FPD 4 are moved immediately after the X-ray emission completes. The movement has already been described with FIG. 2. That is, the X-ray tube 3 and the FPD 4 located at the positions denoted by dashed-dotted lines in FIG. 2 are moved to the positions denoted by dotted line after X-ray emission for taking an original image P0a, and then an original image P0b is obtained. Then after the X-ray emission for taking the original image P0b, the X-ray tube 3 and the FPD 4 in the positions denoted by dotted lines are moved to the positions denoted by solid lines, whereby an original image P0c is obtained. The obtained original images P0a, P0b, and P0c are transmitted to the long-length image generating unit 12. The long-length image generating unit 12 combines the original images P0a, P0b, and P0c to generate a long image P1. The display unit 39 displays the generated long image P1, whereby the long-length radiography completes.

As noted above, with the X-ray apparatus according to Embodiment 1, successive imaging is performable while the timing to activate the X-ray tube 3 in a rest state is acquired appropriately. That is, with the configuration of Embodiment 2, the difference time is calculated by subtracting the time width of the activation time period from the time width of the non-detectable time period, and the time after the difference time has elapsed from the X-ray emission is determined as a timing to activate the X-ray tube 3. Here, the time width of the non-detectable time period is a time width from when the FPD 4 detects X-rays one time to when posterior X-ray detection is performable. The time width of the activation time period is a time width from activate to completion of activation of the X-ray tube 3. The X-ray tube 3 is activated at the timing with Embodiment 2, whereby end of the non-detectable time period of the detector conforms to end of the time period for activating the X-ray tube 3. This ensures rapid successive imaging while the activation of the X-ray tube 3 and preparation of the detector are performed simultaneously. Moreover, in Embodiment 2, the X-ray tube 3 is in a rest state during X-ray emission. In contrast to this, in the conventional automatic type in FIG. 12, the X-ray tube 3 is activated all the time once the successive imaging is activated. In other words, in the conventional automatic mode, the filament in the X-ray tube 3 is always kept at high temperatures, causing readily damages on the filament. As noted above, Embodiment 2 achieves a longer life of the X-ray tube 3 than that in the conventional type.

The present invention is not limited to the above embodiments, but may be modified as under.

(1) In addition to the configurations mentioned above, the notifying unit 36 may count down the timing before the difference time elapses when the emission instruction is provided through the operation switch 38. In this case, the given time period T1 as a standby time from completion of the X-ray emission should be shortened by time required for the count down. The notifying unit 36 provides notification that the timing for the timing determining unit 17 has arrived through the count down, whereby the operator can provide the instructions more easily. Any time point within a time period after the given time period T1 has elapsed from the X-ray emission is selectable as a timing to activate the count down. Consequently, the time period of the countdown should not be longer than the given time period T1.

(2) Moreover, the notifying unit 36 may notify the operator of the instruction after given time delay from the timing provided by the timing determining unit 17. This ensures a sufficient rest time of the X-ray tube 3.

(3) The embodiments of the present invention are not limited to the feature that the X-ray tube 3 is moved along with the FPD 4 during the long-length radiography. Alternatively, the embodiments are applicable to the feature that the X-ray tube 3 inclines relative to the movement of the FPD 4.

(4) The embodiments of the present invention are not imitatively applicable to the long-length radiography. Alternatively, the embodiments are applicable to radiography in which successive imaging is performed to the subject M while the X-ray tube 3 and the FPD 4 are not moved.

(5) A function of switching between the manual mode in Embodiment 1 and the automatic mode in Embodiment 2 through operator's decision may be added to the embodiments of the present invention.

Industrial Applicability

As noted above, the above invention is suitable in medical fields.

REFERENCE SIGN LIST

3 X-ray tube (radiation source)
4 FPD (detecting device or means)

6 X-ray tube controller (radiation source controller)
11 image generating unit (image generator)
12 long-length image generating unit (long-length image generator)
17 timing determining unit (determining device or means)
18 difference time calculating unit (difference time calculating device or means)
36 notifying unit (notifying device or means)
37 storing unit (storing device or means)
38 operation switch (activation instruction input device or means)
38 operation switch (emission instruction input device or means)

It will be further understood that the enclosed devices, systems, apparatus, module, and means herein, it will be expressly understood that the phrase 'means' in the specification does not create a 'means for' presumption, and any presumption is expressly rebutted here stating that unless expressed in an exact 'means for' language there is no assertion of §112¶6 presumption within the lexicography of the applicant, the structure noted herein would include the understood structure, processors, processing boards, memory and other electronic devices discussed herein to achieve the stated function and not external to this disclosure.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

The invention claimed is:

1. A radiographic apparatus, comprising:
   a radiation source emitting a radiation during a use as an activated radiation source, and changing into a rest state after a one-time emission of said radiation;
   a detector of radiation, the detector requiring an interval time between a first detection and a next detection of the detector;
   an image generator generating a plurality of images in accordance with said first detection and a next detection of the detector;
   an activation instruction input apparatus operable to input an activation instruction to the radiation source in the rest state;
   an emission instruction input apparatus operable to cause an input radiation emission instruction to the activated radiation source;
   a storing device operable to store a time width of an activation time period as a time period required for activating the radiation source and a time width of a non-detectable time period that the detector requires between detection and next detection;
   a difference time calculating apparatus operable to subtract the time width of the activation time period from the time width of the non-detectable time period; and
   a determining apparatus operable to determine during said use that a timing to activate the radiation source in the rest state has arrived after the calculated difference time elapsed from the radiation emission means.

2. The radiographic apparatus according to claim 1, further comprising:
   a notifying apparatus operative during said use to notify an external operator of arrival of the timing determination.

3. The radiographic apparatus according to claim 2, wherein:
   the notifying apparatus is operative to provide a visible display to said external operator.

4. The radiographic apparatus according to claim 2, wherein:
   the notifying apparatus is operative to provide a sound to said external operator.

5. The radiographic apparatus according to claim 2, wherein:
   the notifying device is operative to count down a timing before the difference time elapses if the emission instruction input apparatus provides the radiation emission instruction.

6. The radiographic apparatus according to claim 2, further comprising:
   a long-length image generator operative to generate a long-length image by combining a series of images generated by said radiographic apparatus while the detector is moved relative to a target.

7. The radiographic apparatus according to claim 1, further comprising:
   a radiation source controller operative to activate an instruction to the radiation source when the timing arrives.

* * * * *